United States Patent [19]

Hijikata

[11] 4,224,405
[45] Sep. 23, 1980

[54] METHOD AND APPARATUS FOR DETERMINING THE RATE OF ENZYME REACTION

[75] Inventor: Kazuo Hijikata, Hachioji, Japan

[73] Assignee: Olympus Optical Co., Ltd., Tokyo, Japan

[21] Appl. No.: 900,149

[22] Filed: Apr. 26, 1978

[30] Foreign Application Priority Data

May 10, 1977 [JP] Japan ................... 52/53596

[51] Int. Cl.² .................... C12Q 3/00; C12M 1/40; C12M 1/38
[52] U.S. Cl. .................... 435/3; 23/230 B; 356/409; 356/436; 364/497; 364/499; 364/500; 422/68; 435/4; 435/288; 435/290; 435/291
[58] Field of Search ............... 195/103.5 R, 127, 139; 422/68; 356/409, 414, 436; 364/497, 498, 499, 500; 23/230 B; 435/3, 4, 288, 289, 290, 291, 808

[56] References Cited

U.S. PATENT DOCUMENTS

| | | |
|---|---|---|
| 3,554,654 | 1/1971 | Paatzsch et al. ................ 356/180 |
| 3,578,404 | 5/1971 | Walles et al. ................... 422/68 X |
| 3,706,499 | 12/1972 | Rapoza et al. .................. 356/414 |
| 3,844,661 | 10/1974 | Birkett et al. ................. 356/436 X |
| 3,878,049 | 4/1975 | Tannenbaum et al. ........ 195/103.5 R |
| 4,012,199 | 3/1977 | Luzer ........................... 422/68 X |

FOREIGN PATENT DOCUMENTS

25191 3/1976 Japan.
108885 9/1976 Japan.

Primary Examiner—Robert J. Warden
Attorney, Agent, or Firm—Ostrolenk, Faber, Gerb & Soffen

[57] ABSTRACT

The rate of enzyme reaction is determined by determining of the quantity of enzyme, and deriving the rate of reaction per unit time of a reaction solution having an absorbance which is proportional to the time. A temperature correction coefficient which is used during the determination of the enzyme quantity is derived by temperature information which is supplied by a temperature sensor disposed within the reaction solution to be determined. An apparatus used for the determination of the rate of reaction comprises a means for containing the reaction solution, a temperature sensor directly disposed within the solution, a photoelectric transducer element responsive to light transmitting through the solution to determine the optical density of the solution, a logarithmic conversion circuit which converts the signal from the element into a corresponding absorbance signal, and a coefficient conversion circuit which is responsive to the combination of the absorbance signal and temperature information from the temperature sensor to correct a temperature coefficient.

7 Claims, 5 Drawing Figures

METHOD AND APPARATUS FOR DETERMINING THE RATE OF ENZYME REACTION

BACKGROUND OF THE INVENTION

The invention relates to a method of and apparatus for determining the rate of enzyme reaction, and more particularly, to such method and apparatus in which the quantity of enzyme in a blood sample is determined by a chemical reaction.

Enzyme represents an organic, high polymer catalyst which is present in biological bodies and which is involved with almost every chemical reaction which takes place within the biological bodies. The quantity of enzyme contained in a blood sample cannot be directly determined and is usually determined by an alternative method in which coenzyme is mixed with a collected blood sample and the absorbance of the coenzyme determined to represent a corresponding quantity of enzyme. Specifically, the quantity of enzyme is derived from the rate per unit time of catalyzed reaction. Such determination of the quantity of active enzyme in a blood sample is commonly referred to as the determination of initial rate of chemical reaction, the determination of activity of enzyme, or the determination of rate of enzyme reaction.

An apparatus used for such determination is arranged to maintain a proportional relationship between the absorbance and the time so that a change thereof can be utilized to determine the enzyme quantity. Specifically, the enzyme quantity IU per liter is determined as follows.

$$IU/l = \Delta A/\min \times K \quad (1)$$

where $$K = V_t \times V_f \times 1000/V_s \times C$$

and wherein l represents a liter of blood, $\Delta A/\min$ a difference in the absorbance (optical density) per minute, $V_f$ the overall volume, $V_s$ the volume of sample, $V_t$ a temperature correction coefficient and C a factor which relates to the determination of a coenzyme at a given optical wavelength.

The equation (1) can be rewritten as follows:

$$IU/l = \Delta A/\min \times K' \times V_t \quad (2)$$

where $$K' = V_f \times 1000/V_s \times C$$

Thus it is seen that the enzyme quantity is a function of the temperature.

The difference in the absorbance $\Delta A$ can be determined by an optical determination of the initial rate of reaction. Specifically, a reagent is introduced into a reaction solution contained in a reaction vessel, and an initial rate of change per unit time in the absorbance of the reaction solution is considered as representing the degree of reaction. Referring to FIG. 1, where the abscissa represents the reaction time t and the ordinate the optical density (O.D), several curves are shown each of which represent the variation of the density which occurs when the reagent is introduced. The initial rate referred to above is represented by changes $\Delta E_1$, $\Delta E_2$, $\Delta E_3$ in the absorbance per one minute $\Delta t$ measured along the initial portion of the linear segment of the curves.

In the apparatus which determines the rate of enzyme reaction, the temperature of the reaction solution is maintained constant by a temperature control of a thermostat so that a fixed value of temperature correction coefficient appearing in the equations (1) and (2) can be used. A first prior art arrangement for this purpose is shown in FIG. 2 where a glass vessel 1 contains a thermostat liquid 2 which is heated by a heater 3. A temperature sensor 4 is introduced into the body of the thermostat liquid to determine the temperature thereof so that the liquid can be maintained at a constant temperature through an automatic control of the heater 3. A cell 5 containing a reaction solution 6 is immersed into the thermostat liquid 2, and an optical flux P of a given optical wavelength is passed therethrough to determine the absorbance.

FIG. 3 shows a second prior art arrangement in which a thermostat block 7 is adapted to be heated by a heating element 8, which is automatically controlled by a temperature sensor 9 in order to maintain the block 7 at a constant temperature. A reaction solution 10 is contained in a cell 11, which is fitted into the block 7. The block 7 is formed with a pair of aligned openings 7a, through which the optical flux P is passed to determine the absorbance.

With the conventional arrangements, it is not possible to achieve a satifactory temperature control of the reaction solution with time or as the ambient temperature changes. It is to be noted that the temperature control of the reaction solution represents an important factor in the determination of the reaction rate, and if the temperature of the reaction solution changes by 1° C., the resulting influence upon the final data will be as much as 10%. It is also to be noted that even if the accuracy of the temperature control is improved as desired, this does not result in improving the accuracy of the temperature control of the reaction solution contained in the cell since the control has been directed to the thermostat itself. Thus, if a reagent is introduced into the reaction solution, there immediately results a reduction in the temperature of the reaction solution. It will thus be seen that the determination has been conducted in the prior art arrangement under the reduced temperature condition.

SUMMARY OF THE INVENTION

It is an object of the present invention to provide a method for determining the rate of enzyme reaction which eliminates the described disadvantages of the prior art by employing a direct measurement of the temperature of the reaction solution and by utilizing resulting temperature information to provide a correction of data obtained about the enzyme quantity so that correct data can be obtained free from the influence of temperature changes without requiring a close temperature control of a thermostat.

It is another object of the invention to provide an apparatus for determining the rate of enzyme reaction which is optimally adapted to carry out the method described in the preceding paragraph.

In accordance with the invention, it is unnecessary to maintain the temperature of the reaction solution being determined at a constant temperature, but the temperature of the solution is allowed to vary. However, the variation of temperature is reflected in deriving the final data concerning the enzyme quantity. In this manner, the enzyme quantity can be very accurately determined. Since a close temperature control of the thermostat block is not required, temperature control can be greatly simplified over the prior art arrangement.

DESCRIPTION OF PREFERRED EMBODIMENT

Figure 1:
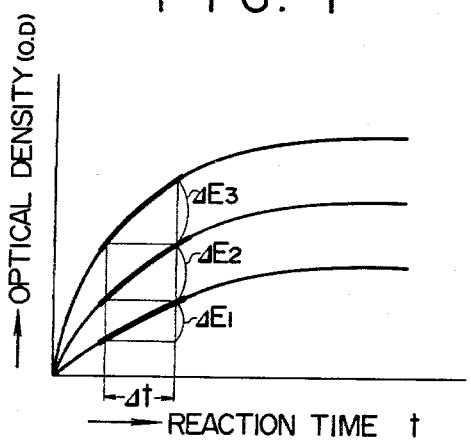
FIG. 1 graphically shows the optical density plotted over the reaction time, illustrating that the absorbance is represented by the initial rate.
Figure 2:
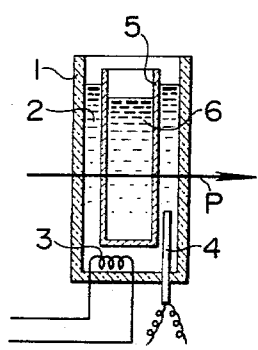
FIGS. 2 and 3 are schematic cross sections of conventional thermostats used in the determination of rate of enzyme reaction.
Figure 3:
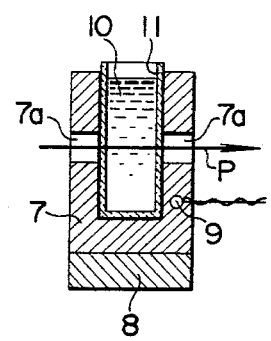
Figure 4:
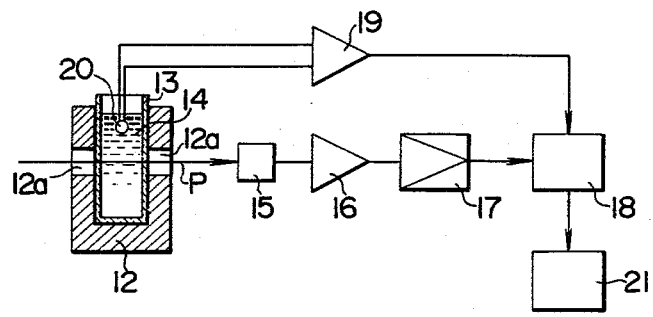
FIG. 4 is a schematic cross section of a thermostat block in combination with a block diagram of the arrangement used to carry out the method of the invention.

Referring to FIG. 4, there is shown a general arrangement of an apparatus for determining the rate of enzyme reaction which is constructed in accordance with the present invention. A thermostat block 12 internally houses a transparent cell 13 which contains a quantity of reaction solution 14. The block 12 is formed with a pair of aligned openings 12a, through which an optical flux P of a given optical wavelength is passed to determine the density of the solution. After passing through the reaction solution 14, the flux P impinges on a photoelectric transducer element 15 which may comprise a silicon blue cell or the like. The element 15 produces a differential absorbance signal, which is fed to an amplifier 16 before it is input to a logarithmic conversion circuit 17 of a known form. The output of the conversion circuit 17 is supplied to a coefficient conversion circuit 18 which performs the calculation of $\Delta A/\min \times K$.

A temperature sensor 20 such as a thermistor is directly immersed into the reaction solution 14. To minimize the contamination effect, the sensor 20 has its surface treated to be repellent to water as by providing a Teflon coating thereon. It will be understood that any remainder of the blood adhering to the wall surface of the cell 13 which has been used during the previous measurement cycle can be removed by rinsing the cell 13, thus preventing its admixture and contamination of a fresh blood sample next introduced into the cell 13. The purpose of the repellent treatment of the temperature sensor 20 is to prevent a similar contamination of the fresh blood sample by the old blood sample which may remain attached thereto. Temperature output from the sensor 20 is fed through an amplifier 19 to the coefficient conversion circuit 18.

Figure 5:
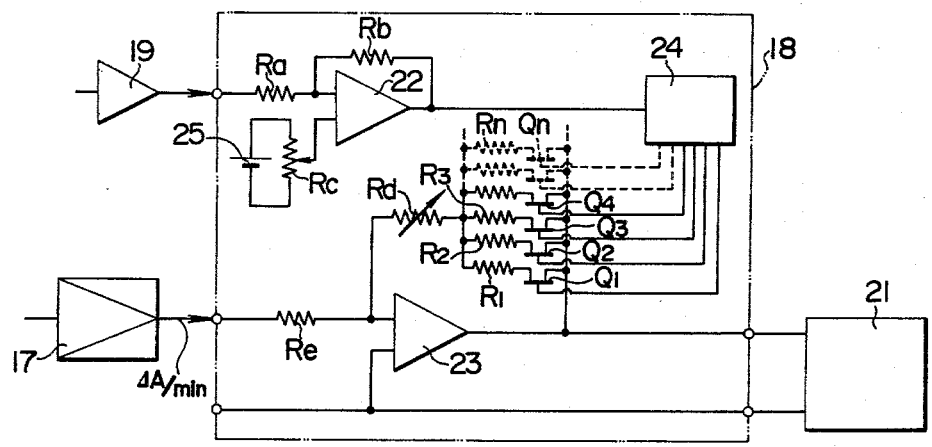
FIG. 5 is a circuit diagram of a coefficient conversion circuit shown in FIG. 4.

As shown in FIG. 5, the coefficient conversion circuit 18 comprises an analog calculation circuit of a conventional form which includes operational amplifiers 22, 23, A/D converter 24, FET's Q1 to Qn, resistors Ra to Re and R1 to Rn, and a bias source 25. The combination of bias source 25 and resistor Rc supplies a suitable bias voltage to the amplifier 22, which is fed with a temperature output from the amplifier 19. The output of the amplifier 22 is supplied to A/D converter 24. The plurality of FET's Q1 to Qn are connected with respective output terminals of A/D converter, and the output terminal of the transistors is connected with individual resistors R1 to Rn. The opposite ends of resistors R1 to Rn are connected together and with the input of amplifier 23 through resistor Rd. The output of the conversion circuit 17 is applied to the same input terminal of the amplifier 23 through resistor Re, and the output of amplifier 23 is connected with individual gates of the respective FET's and also with an output printer 21.

In the use of the apparatus, the cell 13 containing the reaction solution or blood sample 14 to be analyzed is received in the thermostat block 12 which is maintained at a constant temperature. Subsequently, the sensor 20 is inserted into the solution 14, the sensor being preferably constructed to have a reduced heat capacity. A reagent is introduced into the reaction solution 14, and after a time period of about 30 seconds, the flux P of the given wavelength is passed through the openings 12a and through the reaction solution 14. A chemical reaction occurs between the reaction solution 14 and the reagent, producing a change in the optical density thereof with time. The change of the absorbance over a time interval of one minute is measured. The flux P impinges on the element 15, which converts it into a corresponding electrical signal. The conversion circuit 17 converts it into a corresponding logarithmic signal, which is input to the coefficient conversion circuit 18.

The sensor produces a temperature output and supplies it through the amplifier 19 to the coefficient conversion circuit 18. In response to the temperature signal, A/D converter 24 in the circuit 18 renders FET's Q1 to Qn conductive in accordance with the temperature information, supplying a corresponding input to the amplifier 23. In this manner, the temperature correction coefficient $V_t$ is changed in accordance with the temperature of a reaction solution to assure an accurate value of the enzyme quantity IU which is outputted from the amplifier 23. The corrected data is printed out by the printer 21.

The correction scheme described above improves the accuracy of the value of enzyme quantity IU over that obtained with the prior art arrangement.

While the coefficient conversion circuit 18 has been constructed as an analog circuit in the embodiment described above, it may be replaced by the function of a computer or center processing unit including a memory in which varying values of the coefficient for temperature changes are stored and read out in accordance with an output from the A/D converter, thus calculating $\Delta A/\min \times K$ or the enzyme quantity IU.

What is claimed is:

1. A method of determining the rate of an enzyme reaction in which an enzyme quantity is determined from the rate of a reaction in a reaction solution having an absorbance changing approximately linearly with the time; said method comprising the steps of:
    disposing a temperature sensor in the reaction solution for measuring the temperature thereof;
    modifying the value of a temperature correction coefficient in accordance with temperature information from said sensor to correct for temperature changes in said reaction solution; and
    using said value of said temperature correction coefficient to determine the rate of said enzyme reaction.

2. An apparatus for determining the rate of an enzyme reaction, comprising:
    reaction solution container means for containing a quantity of a reaction solution and including a transparent portion which permits light to pass through said reaction solution contained therein;
    a temperature sensor disposed in a position inside said container means and in direct contact with said reaction solution when said transparent cell contains said reaction solution for measuring the temperature thereof;

a photoelectric transducer element responsive to light which is passed through said solution;

a logarithmic conversion circuit for converting an electrical signal generated by said transducer element into a signal indicative of the absorbance of said reaction solution; and a coefficient conversion circuit for modifying a temperature correction coefficient used in the determination of the enzyme quantity responsive to both said signal from said logarithmic conversion circuit and temperature information from said temperature sensor.

3. An apparatus according to claim 2 in which said temperature sensor comprises a thermistor having its surface provided with a coating of a water-repellent-material to prevent contamination.

4. An apparatus according to claim 2 in which said coefficient conversion circuit comprises:

an amplifier for amplifying said signal generated by said temperature sensor;

an analog-digital converter having a plurality of outputs for converting the output generated by said amplifier into corresponding digital signals;

a plurality of field effect transistors equal in number to said plurality of outputs and having their respective gate electrodes connected with respective individual ones of said outputs of aid analog-digital converter so as to be rendered conductive responsive to said digital signals, and a second amplifier connected in series with each of said transistors and also receiving a signal generated by said logarithmic conversion circuit.

5. An apparatus according to claim 2, wherein said reaction solution containing means further comprises a transparent cell for containing said reaction solution.

6. An apparatus according to claim 5, wherein said reaction solution containing means further comprises a thermostatic block accommodating said transparent cell.

7. An apparatus according to claim 2, further comprising output printer means for printing data representative of the output of said coefficient conversion circuit.

* * * * *